United States Patent [19]
Haber et al.

[11] Patent Number: 4,820,275
[45] Date of Patent: Apr. 11, 1989

[54] RETRACTABLE NEEDLE SYRINGE WITH INTEGRAL SPRING

[75] Inventors: Terry M. Haber, Lake Forest; Clark B. Foster, El Toro; John A. Lewis, Jr., Costa Mesa, all of Calif.

[73] Assignee: Habley Medical Technology Corporation, Laguna Hills, Calif.

[21] Appl. No.: 135,607

[22] Filed: Dec. 21, 1987

[51] Int. Cl.$^4$ .............................................. A61M 5/32
[52] U.S. Cl. .................................... 604/198; 604/232
[58] Field of Search ............... 604/198, 232, 187, 195, 604/196, 194, 193, 136, 156, 197, 138

[56] References Cited

U.S. PATENT DOCUMENTS

| | | | |
|---|---|---|---|
| 2,876,770 | 3/1959 | White | 604/232 X |
| 2,925,083 | 2/1960 | Craig | 604/197 |
| 3,046,985 | 7/1962 | Saenz | 604/197 |

Primary Examiner—John D. Yasko
Attorney, Agent, or Firm—Morland C. Fischer

[57] ABSTRACT

A dental syringe of the type having a pre-filled cartridge of fluid medication and a double ended hypodermic needle communicating with the cartridge for injecting the contents thereof into a targeted tissue area of a patient. The cartridge is carried within an inner syringe cylinder, and the inner cylinder is slideable through an outer syringe cylinder. The inner cylinder has a pair of axially spaced locking grooves which extend around the periphery thereof. The outer cylinder includes a finger ring having an integral, inwardly projecting tab. The finger ring is hingedly connected to the outer cylinder so that the integral tab may be rotated into or out of engagement with either one of the pair of locking grooves of the inner cylinder. With the tab engaging a first of the locking grooves, the inner cylinder is retained at a relatively proximal position within the outer cylinder so that the needle is located inwardly of and completely shielded thereby to prevent an accidental needle strike. With the tab engaging a second of the locking grooves, the inner cylinder is retained at a relatively distal position within the outer cylinder so that the needle is extended outwardly thereof for administering an injection. A coil spring surrounds the inner cylinder for automatically biasing the inner cylinder and hypodermic needle towards the shielded proximal position within the outer cylinder.

20 Claims, 4 Drawing Sheets

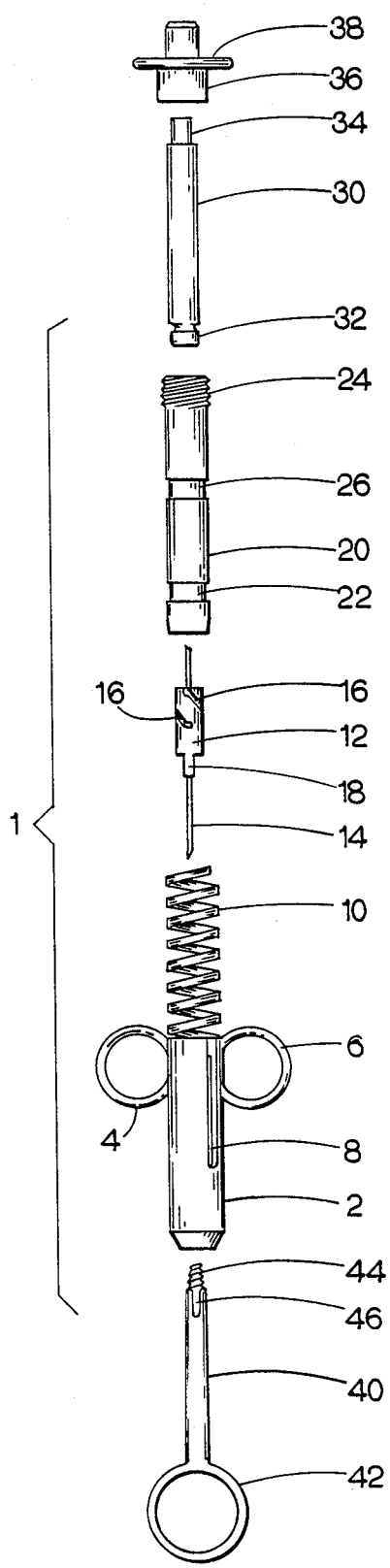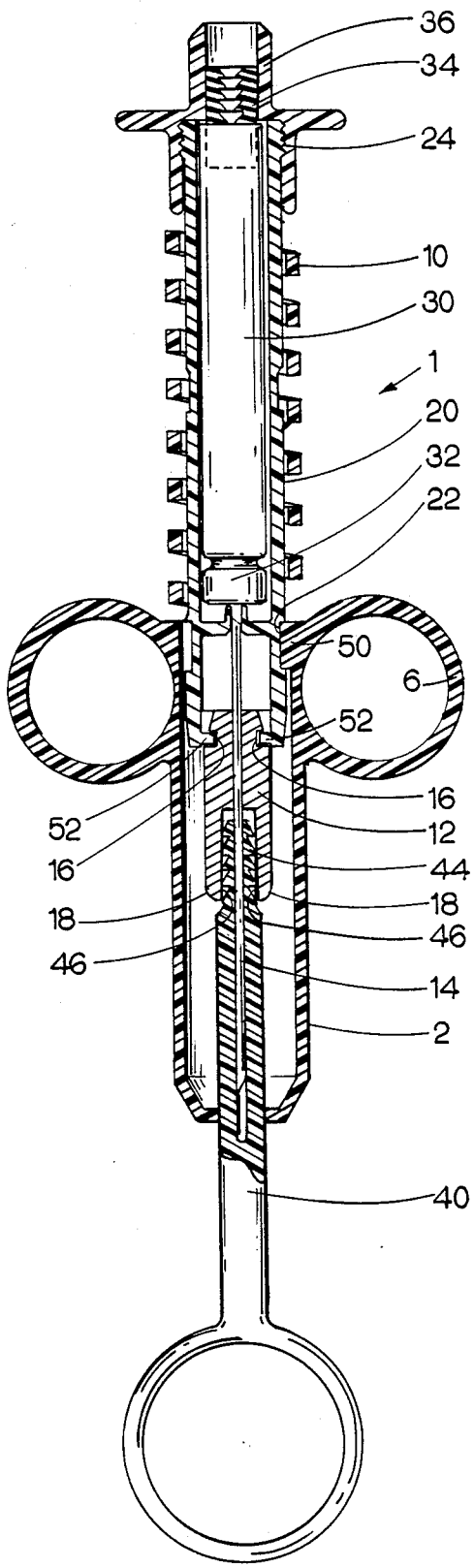
FIG 1
FIG 2

RETRACTABLE NEEDLE SYRINGE WITH INTEGRAL SPRING

BACKGROUND OF THE INVENTION

1. FIELD OF THE INVENTION

This invention relates to a dental syringe of the type having a pre-filled cartridge of fluid medication and a double ended hypodermic needle which may be automatically relocated from a distally extended position, at which to inject the fluid medication into a targeted tissue area, to a proximally retracted position, at which the needle is withdrawn into and shielded by the cylinder of the syringe.

2. PRIOR ART

Dental syringes of the type having a pre-filled cartridge of fluid medication and a double ended hypodermic needle are well-known in the art for injecting such medication from the cartridge to a targeted tissue area of a patient. However, at the completion of the injection, the needle is typically locked in an axially extended position projecting outwardly from a distal bore formed through the syringe cylinder.

In some cases, the syringe may be used to treat a patient having a communicable disease. Prior to disposing the syringe, the hypodermic needle is frequently broken or destroyed to prevent reuse. Dental office workers are especially susceptable to accidental and potentially infectious needle strikes due to the careless handling or breaking of the needle and disposing of the syringe after use. The resulting mini-accident caused by an accidental needle strike typically requires a blood test for such diseases as AIDS and hepatitis. The corresponding cost and inefficiency of testing dental office workers who have received such an accidental needle strike result in considerable waste, which may be particularly damaging to a dental facility which is striving for economy.

The following patent applications, which are assigned or will be assigned to the assignee of the present patent application, disclose syringes having a pre-filled medication cartridge and a needle which is retractable within the syringe cylinder: U.S. Pat. No. 4,767,413 issued Aug. 30, 1988 and entitled DENTAL SYRINGE HAVING AN AUTOMATICALLY RETRACTABLE NEEDLE; and application Ser. No. 101,251 filed Sept. 25, 1987 and entitled DISPOSABLE, PRE-STERILIZABLE SYRINGE FOR A PRE-FILLED MEDICATION CARTRIDGE.

SUMMARY OF THE INVENTION

In general terms, the present invention relates to a reusable syringe of the type having a pre-filled fluid medication cartridge, such as a dental syringe. The syringe includes a hollow outer cylinder having open proximal and distal ends. A hollow inner cylinder is received in and slideable through the outer cylinder. A coil spring is integrally connected to the proximal end of the outer cylinder and positioned so as to surround the inner cylinder. The medication cartridge is carried within the inner cylinder. A needle carrier supports a double ended hypodermic needle for movement through the outer cylinder ahead of the inner cylinder. The needle carrier is connected to and slideable relative to the inner cylinder, so that the distal end of the double ended needle may penetrate the medication cartridge.

The inner cylinder has a pair of axially spaced locking catches (i.e. grooves) formed around the periphery thereof. The outer cylinder has a pair of finger rings extending from opposite sides thereof. One of the finger rings has an integral, inwardly projecting tab. Said finger ring is hingedly connected to the outer cylinder so that the tab thereof can be selectively rotated into or out of either one of the pair of locking catches to retain the inner cylinder at a relatively proximal or distal position within the outer cylinder.

A detachable, hollow needle sheath extends through the open distal end of the outer cylinder to surround and protect the distal end of the double ended needle. The needle sheath may be removed from the needle and connected through the open proximal end of the outer cylinder at a receptacle formed in a piston of the medication cartridge. The needle sheath thereby functions as a piston stem for driving the piston through the medication cartridge to expulse the fluid contents thereof.

In operation, an axial force is first applied to the needle sheath to move the needle carrier proximally through the outer cylinder and toward the inner cylinder. Thus, the proximal end of the needle will penetrate the medication cartridge within the inner cylinder. The needle sheath is then removed through the distal end of the outer cylinder and connected through the proximal end at the receptacle within the piston of the medication cartridge. At the same time that the needle sheath (i.e. stem) is connected to the piston, the integral tab of the finger loop is rotated into the first of the pair of locking catches of the inner cylinder to retain the inner cylinder and the distal end of the hypodermic needle at a relatively proximal position within the outer cylinder. The integral tab of the finger loop is rotated out of the first locking catch, and the inner cylinder is driven axially through the inner cylinder to a relatively distal position at which the coil spring is compressed and the distal end of the needle extended outwardly from the outer cylinder for administering an injection. The tab of the finger ring is then rotated into the second locking catch of the inner cylinder for retaining the inner cylinder at the distal position within the outer cylinder, while an axial force is applied to the piston stem for driving the piston through the medication cartridge to expulse the contents thereof via the needle. Next, the tab of the finger ring is rotated out of the second locking catch, such that the potential energy stored when the coil spring is compressed automatically drives the inner cylinder, the needle carrier and the needle supported thereby back to the proximal position within the outer cylinder. Accordingly, the needle is safely retracted into the outer cylinder so as to be completely surrounded and shielded, whereby to avoid an accidental needle strike during handling and disposing of the syringe.

BRIEF DESCRIPTION OF THE DRAWINGS

FIG. 1 shows an exploded view of the syringe of the present invention;

FIG. 2 shows the syringe of FIG. 1 in an assembled configuration with a double ended hypodermic needle arranged in spaced axial alignment with a medication cartridge;

DESCRIPTION OF THE PREFERRED EMBODIMENT

Figure 5:
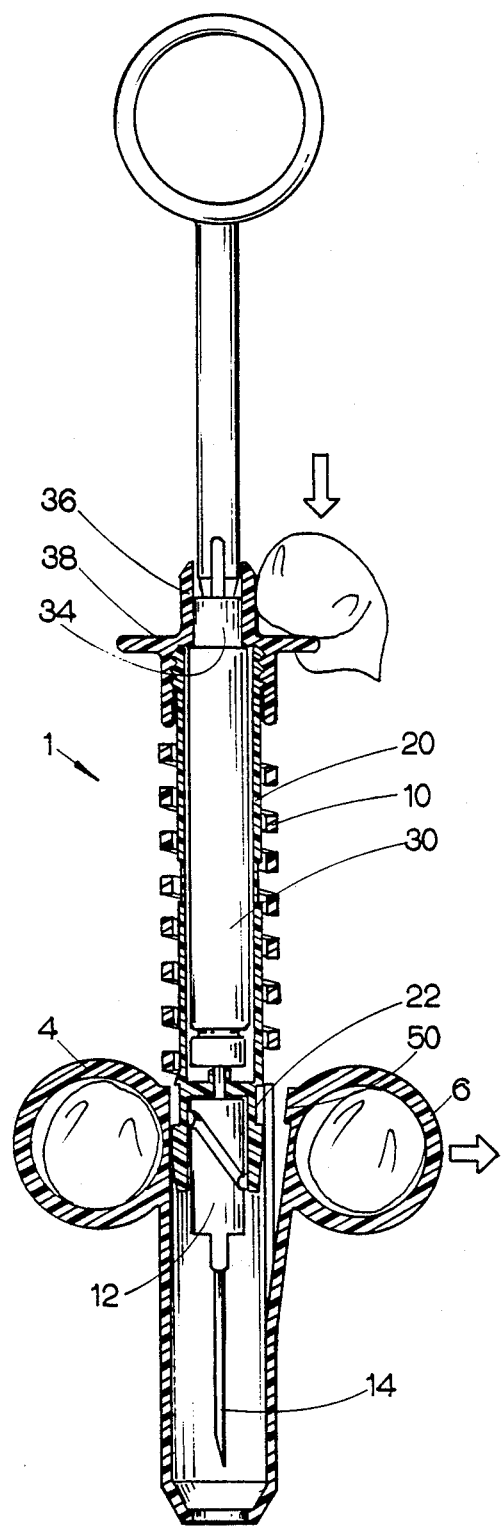
FIG. 5 shows the needle relocated to an axially extended position projecting outwardly from the outer syringe cylinder for administering an injection.
Figure 6:
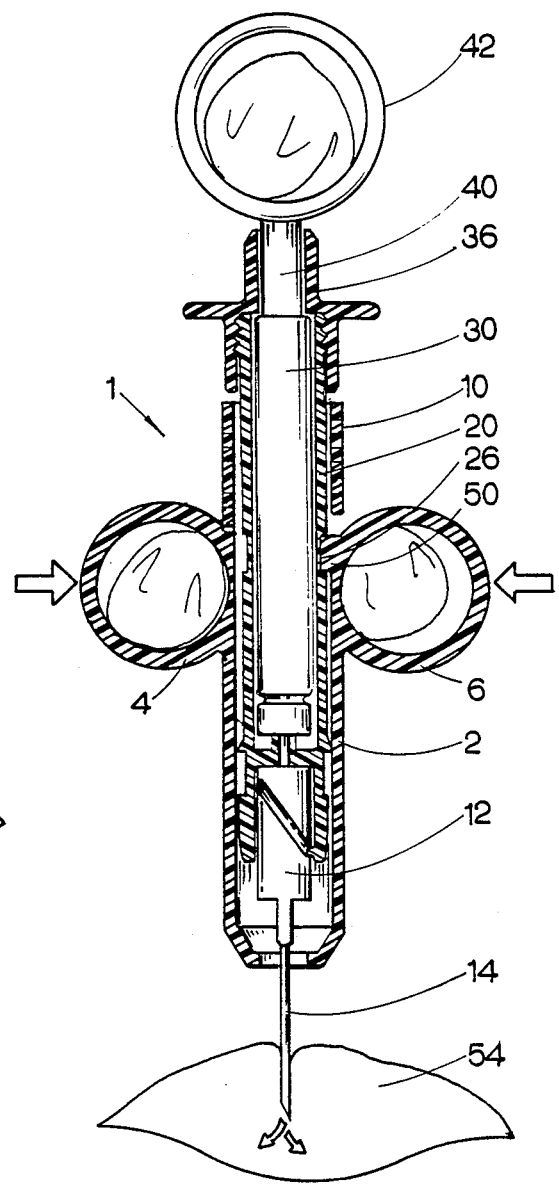
FIG. 6 shows the needle sheath (i.e. piston stem) of FIG. 4 driving the piston through the medication cartridge for expulsing the contents thereof via the needle.

The retractable needle syringe which forms the present invention is now disclosed in detail while referring to the drawings, where in FIG. 1 an exploded view of the syringe 1 is illustrated. Syringe 1 is of the type in which a replaceable medication cartridge or ampule 20 is carried, so that the contents of one or more cartridges may be injected into a targeted tissue area of a patient (as best shown in FIG. 6). Syringe 1 comprises a hollow outer cylinder 2 having open proximal and distal ends. Outer cylinder 2 also has a pair of finger rings 4 and 6 projecting outwardly from opposite sides thereof and a pair of axially extending slots 8 (only one of which is shown) formed at opposite sides of finger ring 6 to form a spring member that is hingedly connected to outer cylinder 2. Thus, finger ring 6 may be rotated relative to cylinder 2 (in a manner that will be described in greater detail when referring to FIG. 5). An integrally connected coil spring 10 projects upwardly from the proximal end of outer cylinder 2 for a purpose which will be disclosed hereinafter.

Syringe 1 includes a cylindrical needle carrier 12 which retains a conventional double ended hypodermic needle 14 in coaxial alignment with outer cylinder 2. Needle carrier 14 is adapted to be moved through outer cylinder 2 so that the proximal end thereof may penetrate the medication cartridge 30 and the distal end can deliver the contents of cartridge 30 to a targeted tissue area of the patient. The needle carrier 12 has a pair of parallel aligned, spiral threads 16 and a pair of oppositely disposed, distally projecting fingers 18 (only one of which is shown), whereby carrier 12 may be interconnected between a needle sheath 40 and an inner cylinder 20.

Syringe 1 also includes a hollow, open ended inner cylinder 20 in which to receive a medication cartridge 30 (best shown in FIG. 2). As will soon be described, inner cylinder 20 is slideable through the outer cylinder 2 to relocate the needle 14 relative to outer cylinder 2 between a retracted position and an axially extended position. Inner cylinder 20 has a distal locking groove or catch 22 formed around the distal end thereof, a set of screw threads 24 formed around the proximal end, and an intermediate locking groove or catch 26 formed between distal catch 22 and screw threads 24.

Cartridge 30 is typically formed of a transparent material (e.g. glass) and is pre-filled with a fluid medication, such as novacaine, or the like. Cartridge 30 has a metal end cap 32 to secure a rubber seal (not shown) across the distal end thereof and a rubber piston 34 received in and movable through the proximal end. Piston 34 includes a hollow threaded receptacle (best illustrated in FIG. 2) so that a screw threaded piston stem 40 may be connected thereto, for driving the piston through the cartridge 30 and thereby expulsing the fluid contents thereof via needle 14.

A hollow, tubular end cap 36 is connected across the proximal end of syringe 1 to retain the medication cartridge 30 within inner cylinder 30. More particularly, end cap 36 has an internal screw thread (best illustrated in FIG. 2) which is adapted to be mated to the threaded end 24 of inner cylinder 20 to prevent the inadvertent removal of cartridge 30 and permit inner cylinder 20 and cartridge 30 to slide in unison through outer cylinder 2. A flange 38 extends around the periphery of end cap 36 to facilitate the process of relocating the needle 14 to the axially extended position relative to cylinder 2 for administering an injection (as is best illustrated in FIG. 5).

A combination needle sheath and piston stem 40 is initially located at the distal end of syringe 1. More particularly, the needle sheath 40 includes an elongated, hollow body having a finger ring 42 located at one end and a screw thread 44 formed at the opposite end thereof. As will soon be described, the hollow needle sheath 40 is extended through the open distal end of outer cylinder 2 to surround the distal end of needle 14. Needle sheath 40 also includes a pair of short, oppositely disposed slots 46 (only one of which is shown) that extend axially from the threaded end 44. As will also soon be explained while referring to FIG. 2, the distal projecting fingers 18 of needle carrier 12 are adapted to be press fit within respective slots 46, so that the carrier 12 and the needle 14 supported thereby can be moved by needle sheath 40 proximally through outer sleeve 2 and towards the sealed end cap 32 of medication cartridge 30.

By way of example only, some or all of the outer cylinder 2, integral spring 10, needle carrier 12, inner cylinder 20, end cap 36, and needle sheath/piston 40 are formed from an optically transparent and generally resilient material, such as polycarbonate, or the like.

FIG. 2 of the drawings shows the syringe 1 of FIG. 1 in an assembled configuration. One example is now provided of an efficient technique by which the configuration of FIG. 2 may be achieved. However, the specific order in which the component parts of syringe 1 are assembled is not to be considered a limitation of the present invention. Initially, the needle carrier 12 is connected to the open distal end of inner cylinder 20. More particularly, a pair of coextensive, inwardly projecting and oppositely disposed teeth 52 are formed at the distal end of inner cylinder 20. The teeth 52 are adapted to be received within and ride through respective spiral slots 16 formed in the needle carrier 12, whereby needle carrier 12 is both attached to and movable relative to inner cylinder 20.

Next, the medication cartridge 30 is loaded into the inner cylinder 20 through the open proximal end thereof. The hollow end cap 36 is then placed over the piston 34 of cartridge 30 and mated (i.e. screwed) to the screw threaded end of cylinder 20 to prevent the withdrawal and limit the proximal travel of cartridge 30 through cylinder 20.

The inner cylinder 20 (and the needle carrier 12 attached thereto) is now in condition to be inserted through the coil spring 10 and loaded into syringe 1 at the open proximal end of outer cylinder 2. Inner cylinder 20 is moved axially and distally through outer cylinder 2 until a coextensive, inwardly projecting tab 50 of finger loop 6 is received by the distal locking catch 22 of cylinder 20. The receipt of tab 50 by distal catch 22 retains the inner cylinder 20 at a relatively proximal position within the outer cylinder 2.

With the inner cylinder 20 retained at a relatively proximal position within outer cylinder 2, the coil spring 10 assumes a normally relaxed condition between the outer cylinder 2 and the end cap 36. Moreover, the teeth 52 of inner cylinder 20 are initially located at the proximal ends of the spiral slots 16 of needle carrier 12, so that the proximal end of needle 14 is retained in axially spaced alignment with the end cap 32 of medication cartridge 30.

The hollow body of needle sheath 40 is inserted through the open distal end of outer cylinder 2 to surround and protect the distal end of needle 14 at the interior of cylinder 2 and thereby prevent an accidental needle strike and possible contamination of the needle. Moreover, the screw threaded end 44 of needle sheath 40 is received in a close friction fit at the interior of needle carrier 14 to prevent an inadvertent detachment of sheath 40 from needle 14.

Figure 3:
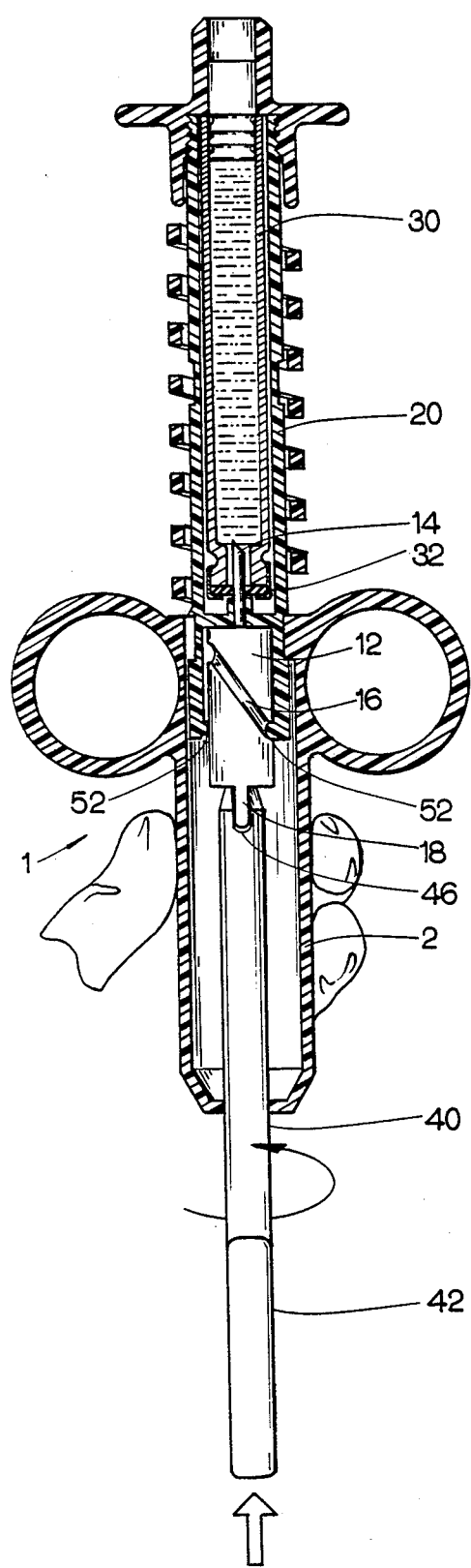
FIG. 3 shows a hypodermic needle communicating with the interior of the medication cartridge.

The operation of the syringe 1 is now described while referring to FIGS. 3–7 of the drawings. In FIG. 3, the proximal end of hypodermic needle 14 is moved into communication with the interior of medication cartridge 30. More particularly, the user grasps the distal end of outer cylinder 2 with one hand and the finger ring 42 of needle sheath 40 with the other hand. An axial force is then applied at the same time that the finger ring 42 is rotated. Accordingly, the slots 46 of needle sheath 40 are pressed into frictional engagement with the distally projecting fingers of needle carrier 12, whereby the rotational and axial forces applied to needle sheath 40 are transferred to needle carrier 12. Thus, needle carrier 12 is caused to rotate, such that the radially projecting teeth 52 of inner cylinder 20 ride through respective spiral slots 16 of needle carrier 12 to cause the carrier (and the needle 14 retained thereby) to be advanced proximally through the outer cylinder 2 and into the inner cylinder 20. In this manner, the proximal end of needle 14 is driven through the seal at the end cap 32 of medication cartridge 30 so as to communicate with the fluid contents thereof.

Figure 4:
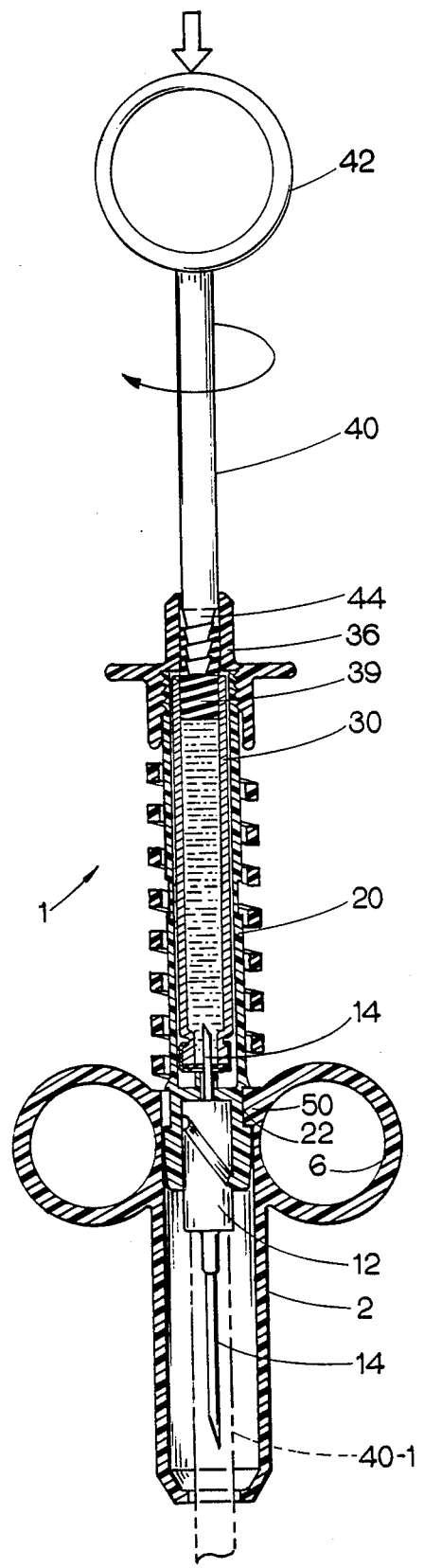
FIG. 4 shows a needle covering sheath detached from the distal end of an outer syringe cylinder and connected to a piston of the medication cartridge at the proximal end of the cylinder.

In FIG. 4, the dual needle sheath/piston stem (designated 40-1 and shown in phantom) is withdrawn from the outer cylinder 2 via the open distal end thereof to unsheath the distal end of needle 14. That is to say, needle sheath 40-1 is withdrawn axially and distally from outer cylinder 2, such that the slots 46 thereof are pulled out of their press fit engagement with the distally projecting fingers 18 of needle carrier 12 (best illustrated in FIG. 3). The needle sheath/piston stem 40 is removed to the proximal end of syringe 1, such that the screw threaded end 44 thereof is inserted through the hollow end cap 36 and into engagement with the screw threaded receptacle of piston 34 at the proximal end of medication cartridge 30.

The user then grips the finger ring 42 of piston stem 40 and applies an axial force at the same time that the ring 42 is rotated (as indicated by the reference arrows). Accordingly, the screw threaded end 44 of piston stem 40 is attached to the screw threaded receptacle end of piston 34 to form an integral piston assembly comprising an elongated piston stem 40 and a piston or plunger head 34. It might be noted that the attachment of the piston stem 40 to piston 34 is facilitated by virtue of the receipt of the inwardly projecting tab 50 of finger ring 6 by the distal locking catch 22 of inner cylinder 20. That is to say, and as previously described when referring to FIG. 2, the receipt of tab 50 in catch 22 retains the inner cylinder 20 at a relatively proximal position within outer cylinder 2. Moreover, the distal end of needle 14 cannot be inadvertently extended outwardly from the outer cylinder 2 when the user applies an axial force to finger ring 42 to attach piston stem 40 to piston 34.

In FIGS. 5 and 6, the needle 14 is advanced from a retracted and shielded position (as illustrated in FIG. 5) to an axially extended position relative to outer cylinder 2 (as illustrated in FIG. 6), so that an injection may be administered. More particularly, and referring initially to FIG. 5, the user places his thumb upon the flange 38 of end cap 36 and his index and middle fingers in respective finger rings 4 and 6. The user then spreads his index and middle fingers, whereby the hinged spring member (formed between the axial slots 8 of outer cylinder 2 of FIG. 1) permits ring 6 to be rotated in a radially outward direction (as indicated by the reference arrow) so that the integral tab 50 of finger ring 6 will be disengaged from the distal catch 22 of the inner cylinder 20. The user uses his thumb to exert an axial force upon the flange 38 of end cap 36 (in the direction of the reference arrow) at the same time that his index and middle fingers pull proximal upon the finger rings 4 and 6 so as to drive the combination of needle carrier 12, inner cylinder 20 and medication cartridge 30, against the normal bias of compression spring 10, distally through the outer cylinder 2.

Accordingly, and referring now to FIG. 6, the spring 10 is compressed (between end cap 36 and outer cylinder 2) and the distal end of needle 14 is correspondingly moved (with needle carrier 12 and inner cylinder 20) through inner cylinder 2 and past the open distal end thereof to the axially extended position. The user continues to drive the inner cylinder 20 through the outer cylinder 2, until the integral tab 50 of finger ring 6 is engaged by the intermediate locking catch 26 of inner cylinder 20. That is, the finger ring 6 is automatically rotated in a radially inward direction (by virtue of memory of the spring to which finger ring 6 is attached) towards inner cylinder 20, so that tab 50 may be received in catch 26.

Next, the user draws his index and middle fingers together in finger rings 4 and 6 (in the direction of the reference arrows), whereby to cause the integral tab 50 of finger ring 6 to be securely positioned within the intermediate locking catch 26 of inner cylinder 20. The inner cylinder 20 is, thereby, retained at a relatively distal position within outer cylinder 2. With the inner cylinder 20 retained at a relatively position and the distal end of needle 14 moved to and held at the axially extended position, the user may expulse the fluid contents of medication cartridge 30. More particularly, the distal end of the needle 14 penetrates the patient's skin at a targeted tissue area 54. The user then relocates his thumb from the flange 38 of end cap 36 (of FIG. 5) to the finger ring 42 of piston stem 40. The user uses his thumb to exert an axial force upon the finger ring 42 (as indicated by the reference arrow) to drive the piston stem 40 and the piston connected thereto (designated 34 in FIG. 5) through the cartridge 30 to thereby inject the medication into the targeted tissue area 54 via needle 14.

Figure 7:
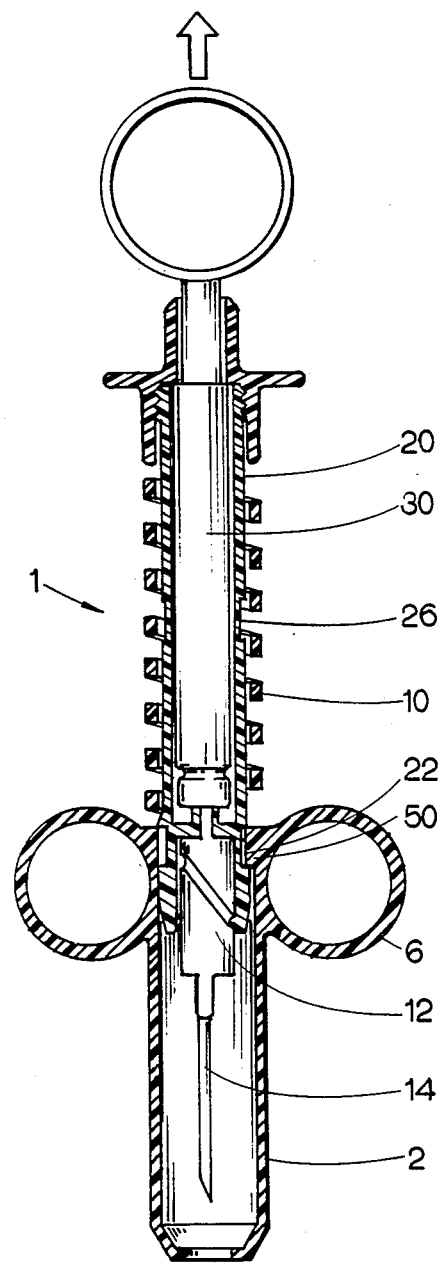
FIG. 7 shows the needle after it is automatically retracted within the outer syringe cylinder so as to be completed surrounded and shielded and thereby avoid an accidental needle strike.

After the cartridge 30 has been emptied and the needle 14 withdrawn from the patient's tissue, the needle is automatically returned to the retracted position within outer cylinder 2. That is, and referring to FIG. 7, the user again spreads his middle and index fingers, whereby to rotate finger ring 6 in a radially outwardly direction (in the manner previously described when referring to FIG. 5), so that integral tab 50 of finger ring 6 will be disengaged from the locking catch 26 of inner cylinder 20. With the tab 50 removed from catch 26, the inner cylinder 20 is once again free to slide through outer cylinder 2. Accordingly, spring 10, which is compressed while inner cylinder 20 is retained at the distal position of FIG. 6, expands back to its normally relaxed condition, such that the stored potential energy of spring 10 will automatically and immediately drive the combination of inner cylinder 20, the now empty medication cartridge 30, and needle carrier 12 axially and proximally through outer sleeve 2 (in the direction of the reference arrows) to the relatively proximal position therewithin. The distal end of needle 14 is thereby relocated from the axially extended position (of FIG. 6) to the retracted position, as shown in FIG. 7, without requiring any additional action on the part of the user. What is even more, the tab 50 of finger loop 6 is moved back into the distal locking catch 22 to retain the inner cylinder 20 at the relatively proximal position, where needle 14 is completely surrounded and shielded by the outer cylinder 2 to avoid an accidental needle strike and prevent the spread of contagious, and possibly life threatening, disease.

Hence, the syringe 1 may be safely handled and discarded after use, or the syringe may be reused to perform multiple injections by replacing the medication cartridge 30. In any event, the presently described retractable needle syringe eliminates the need for dental office workers to either handle or cut the needle prior to disposal, as has heretofore been required with conventional syringes.

It will be apparent that while a preferred embodiment of the present invention have been shown and described, various modifications and changes may be made without departing from the true spirit and scope of the invention. For example, although the syringe 1 of this invention has particular application as a dental syringe, it is to be understood that this is not to be regarded as a limitation, and the claims which are appended hereto are applicable to other syringes which utilize a pre-filled medication cartridge and where it is desirable to relocate a hypodermic needle from a distally extended position to a proximally retracted position relative to the outer cylinder in order to render the syringe safe for handling and/or disposal.

Having thus set forth the preferred embodiment, what is claimed is:

1. A syringe comprising:
   an outer cylinder having open proximal and distal ends:
   an inner cylinder containing a pre-filled medication cartridge and being slideable through said outer cylinder;
   a double ended hypodermic needle adapted to communicate at a first end thereof with the interior of said medication cartridge;
   means for carrying said needle being slideable with said inner cylinder through said outer cylinder;
   a pair of finger retaining means attached to said outer cylinder, at least one of said finger retaining means having a tab projecting therefrom;
   a first locking catch formed in said inner cylinder within which to receive the tab of said at least one finger retaining means for locking said inner cylinder at a relatively distal position within said outer cylinder, such that the second end of said needle projects outwardly from the distal end of said outer cylinder for injecting the contents of said medication cartridge; and
   a second locking catch formed in said inner cylinder within which to receive the tab of said at least one finger retaining means for locking said inner cylinder at a relatively proximal position within said outer cylinder, such that the second end of the needle is located inwardly of and completely shielded by said outer clinder.

2. The syringe recited in claim 1, wherein said needle carrying means and said inner cylinder are movable relative to one another, such that the first end of said needle is arranged in spaced axial alignment with said medication cartridge;
   said syringe further comprising means for advancing said needle carrying means axially through said outer cylinder and into said inner cylinder, such that the first end of said needle penetrates said medication cartridge to communicate with the interior thereof.

3. The syringe recited in claim 2, wherein said inner cylinder has at least one tooth projecting therefrom and said needle carrying means has at least one axially extending slot formed therein, said tooth being received in and slideable through said slot for connecting said inner cylinder to said needle carrying means and permitting said needle carrying means to be moved into said inner cylinder means.

4. The syringe recited in claim 2, wherein the means for advancing said needle carrying means into said inner cylinder is a detachable needle sheath extending through the open distal end of said outer cylinder to surround the second end of said needle.

5. The syringe recited in claim 4, wherein said needle sheath has at least one axial slot and said needle carrying means has at least one axially extending finger, said finger being received in said slot to detachably connect said sheath to said needle carrying means.

6. The syringe recited in claim 4, wherein said medication cartridge has a piston located at one end thereof and a receptacle formed in said piston, said needle sheath being detached from said needle at the distal end of said outer cylinder and connected to the receptacle of said piston for driving said piston through said cartridge to expulse the contents thereof.

7. The syringe recited in claim 1, wherein said first and second catches are first and second locking axially spaced grooves formed in said inner cylinder.

8. The syringe recited in claim 1, further comprising spring means surrounding said inner cylinder and being compressed when said inner cylinder and said needle carrying means are retained by said first locking catch at the distal position within said outer cylinder, the potential energy stored when said spring means is compressed driving said inner cylinder and said needle carrying catch to the proximal piston within said outer cylinder when said first locking means releases said inner cylinder.

9. The syringe recited in claim 8, wherein said spring means is integrally connected at one end thereof to the proximal end of said outer cylinder.

10. The syringe recited in claim 1, wherein said pair of finger retaining means are finger rings, said at least one finger ring having said tab being pivotally attached to said outer cylinder so as to be rotatable into and out of said first and second locking catches.

11. A syringe comprising:
  an outer cylinder having open proximal and distal ends;
  an inner cylinder containing a pre-filled medication cartridge and being slideable through said outer cylinder;
  a double ended hypodermic needle;
  means for carrying said needle, said carrying means being positioned relative to said inner cylinder such that a first end of said double ended needle is arranged in spaced axial alignment with said medication cartridge;
  a detachable needle sheath extending through the open distal end of said outer cylinder for surrounding the second end of said needle and advancing said needle carrying means towards said inner cylinder such that the first end of said needle penetrates said medication cartridge to communicate with the interior thereof;
  means for moving said inner cylinder and said needle carrying means distally through said outer cylinder so that the second end of said needle projects outwardly from the distal end of said outer cylinder for injecting the contents of said medication cartridge when said needle sheath is detached from said second end;
  locking means for releasably retaining said inner cylinder at the distal position within said outer cylinder with the second end of said needle extending outwardly from the distal end thereof; and
  means for moving said inner cylinder from the distal position to a relatively proximal position within said outer cylinder when said locking means releases said inner cylinder, such that the second end of the needle is retracted inwardly of and completely shielded by said outer cylinder.

12. The syringe recited in claim 11, wherein the means for moving said inner cylinder to the proximal position is a coil spring that surrounds said inner cylinder and becomes compressed when said inner cylinder is located at the distal position within said outer cylinder, said spring being integrally attached to the proximal end of said inner cylinder.

13. The syringe recited in claim 11, wherein said medication cartridge has a piston located at one end thereof and a receptacle formed in said piston, said needle sheath being detached from the second end of said needle and connected to said piston at the receptacle thereof for driving said piston through the interior of said cartridge to expulse the contents thereof.

14. The syringe recited in claim 11, further comprising means by which to connect said needle carrying means to said inner cylinder.

15. The syringe recited in claim 11, wherein said needle sheath has at least one slot formed therein and said needle carrying means has at least one axially extending finger, said finger being received in said slot to detachably connect said sheath to said needle carrying means for advancing said needle carrying means towards said inner cylinder and the medication cartridge therewithin.

16. The syringe recited in claim 11, wherein the means for moving said inner cylinder and said needle carrying means distally through said outer cylinder includes an end cap detachably connected to said inner cylinder for retaining said medication cartridge therewithin and for receiving a manually generated, distally directed force thereupon.

17. A syringe comprising:
  an outer cylinder having open proximal and distal ends;
  an inner cylinder containing a pre-filled medication cartridge, said inner cylinder being slideable through said outer cylinder;
  a double ended hypodermic needle;
  means for carrying said hypodermic needle to be moved towards said inner cylinder, such that a first end of said double ended needle penetrates said medication cartridge to communicate with the interior thereof;
  means for moving said inner cylinder distally through said outer cylinder;
  locking means for engaging said inner cylinder when said inner cylinder is moved to a distal position within said outer cylinder, said locking means retaining said inner cylinder at said distal position, such that the second end of said double ended needle projects outwardly from the distal end of said outer cylinder for injecting the contents of the medication cartridge; and
  compression spring means being integrally attached to the proximal end of said outer cylinder for surrounding said inner cylinder, said spring means being compressed when said inner cylinder is moved to and retained by said locking means in the distal position, and said spring means being expanded to automatically move said inner cylinder proximally through said outer cylinder when said locking means disengages said inner cylinder, such that the second end of said needle is retracted inwardly of and completely surrounded by said outer cylinder.

18. The syringe recited in claim 17, further comprising an end cap removably attached to said inner cylinder to retain said medication cartridge therewithin, said compression spring means extending between the proximal end of said outer cylinder and the end cap of said inner cylinder to be compressed therebetween when said inner cylinder is moved to and retained in said distal position.

19. A syringe comprising:
  an outer cylinder having open proximal and distal ends;
  an inner cylinder containing a pre-filled medication cartridge and being slideable axially through said outer cylinder;
  a double ended hypodermic needle adapted to penetrate said medication cartridge such that a first end of said needle communicates with the interior of said cartridge;
  at least one finger positioning means attached to said outer cylinder and movable in an inward direction relative to said outer cylinder; and
  a first locking catch formed in said inner cylinder within which to removably receive said finger positioning means when said finger positioning means is moved in the inward direction, the receipt of said finger positioning means in said first locking catch retaining said inner cylinder and said medication cartridge at a relatively distal position within said outer cylinder such that the second end of said needle projects outwardly from the distal end of said outer cylinder for injecting the contents of said medication cartridge.

20. The syringe recited in claim 19, further comprising a second locking catch formed in said inner cylinder in spaced, axial alignment with said first catch, said second locking catch removably receiving said finger positioning means when said finger positioning means is moved in the inward direction for retaining said inner cylinder and said medication cartridge at a relatively proximal position within said outer cylinder such that the second end of said needle is completely surrounded and shielded by said outer cylinder.

* * * * *